US00PP29789P2

(12) United States Plant Patent
Bacon

(10) Patent No.: US PP29,789 P2
(45) Date of Patent: Nov. 6, 2018

(54) PLUM TREE NAMED 'SUPLUMFIFTYTHREE'

(50) Latin Name: *Prunus salicina*
Varietal Denomination: Suplumfiftythree

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 15/732,682

(22) Filed: Dec. 14, 2017

(51) Int. Cl.
*A01H 5/08* (2018.01)

(52) U.S. Cl.
USPC ..... Plt./184
CPC ..... *A01H 5/0862* (2013.01)

(58) Field of Classification Search
USPC ..... Plt./184
See application file for complete search history.

*Primary Examiner* — Kent L Bell
(74) *Attorney, Agent, or Firm* — Knobbe, Martens, Olson & Bear, LLP

(57) ABSTRACT

A new and distinct plum tree variety, *Prunus salicina*, cv. 'Suplumfiftythree' is characterized by having large, juicy fruit with black skin and red flesh. The fruit of the new variety 'Suplumfiftythree' also has a high Brix:Acid ratio, firm flesh, a mild sweet flavor and a stone that clings to the flesh. The date of ripening of the fruit of the new variety is later than for 'Black Splendor' (unpatented) and earlier than 'Owen-T' (unpatented). The fruit of the new variety 'Suplumfiftythree' is larger than the fruit of 'Black Splendor' and smaller than the fruit of 'Owen-T'.

1 Drawing Sheet

Latin name of the genus and species claimed: *Prunus salicina.*

Variety denomination: 'Suplumfiftythree'.

BACKGROUND AND SUMMARY OF THE INVENTION

This application relates to the discovery and asexual propagation of a new and distinct variety of plum, *Prunus salicina* cv. 'Suplumfiftythree'. The new variety was first originated by hybridization in July 2014 by Terry A. Bacon as breeder number 'PL1687RB'.

The new variety 'Suplumfiftythree' is characterized by having large, juicy fruit with black skin and red flesh. The fruit of the new variety 'Suplumfiftythree' also has a high Brix:Acid ratio, firm flesh, a mild sweet flavor and a stone that clings to the flesh.

The seed parent is 'PL761RB' (unpatented breeding selection), and the pollen parent 'PL674RZ' (unpatented breeding selection). The parent varieties were first crossed in February 2011, with the date of first sowing being February 2012, and the date of first flowering being February 2014. The new plum variety 'Suplumfiftythree' was first asexually propagated by Terry Bacon near Wasco, Kern County, Calif. in February 2015 by dormant grafting.

The new variety 'Suplumfiftythree' is similar to its pollen parent 'PL674RZ' in that the fruit of both varieties has red flesh. The new variety 'Suplumfiftythree' differs from 'PL674RZ' in that the fruit of the new variety has a black skin compared to red-dapple skin for the fruit of 'PL674RZ'. Further, the fruit of the new variety 'Suplumfiftythree' is larger at 140 g compared to 100 g for 'PL674RZ'.

The new variety 'Suplumfiftythree' is similar to its seed parent 'PL761RB' in that the fruit of both varieties has red flesh and black skin. The new variety 'Suplufiftythree' differs from its seed parent 'PL6761RB' in that for the new variety ripening time starts 9 days later than for 'PL761RB'. Further, the fruit of the new variety 'Suplumfiftythree' is larger at 140 g compared to 130 g for 'PL761RB'. The new variety 'Suplufiftythree' also differs from 'PL761RB' in that the brix:acid ratio is 34 for the new variety, compared to 21 for 'PL761RB'.

The fruit of the new variety 'Suplumfiftythree' has similar black skin and red flesh as 'Black Splendor' (unpatented). However, the new variety 'Suplumfiftythree' differs from 'Black Splendor' in that the new variety starts ripening about 7 days later than 'Black Splendor'. In addition, the new variety has larger fruit at about 140 g compared 135 g for 'Black Splendor'. The new variety 'Suplumfiftythree' has a brix of 17 degrees, while 'Black Splendor' has a brix of 14 degrees. The fruit of the new variety 'Suplumfiftythree' has black skin like the fruit of 'Owen-T' (unpatented), but the ripening of the new variety 'Suplumfiftythree' starts about 18 days later than 'Owen-T'. Further, the fruit of the new variety 'Suplumfiftythree' has red flesh compared to yellow flesh for 'Owen-T'.

The new variety 'Suplumfiftythree' has been shown to maintain its distinguishing characteristics through successive asexual propagations by, for example, cuttings and grafting.

BRIEF DESCRIPTION OF THE PHOTOGRAPH

The accompanying color photographic illustration FIG. 1 shows typical specimens of the foliage and fruit of the present new plum variety 'Suplumfiftythree'. The illustration shows the upper and lower surface of the leaves, a view of the fruit as a whole, the stone as a whole, and a sectional view of a fruit divided across its suture plane to show flesh color, pit cavity and the stone remaining in place. The photographic illustration was taken shortly after being picked and the colors are as nearly true as is reasonably possible in a color representation of this type. The photographs depict fruit and vegetative growth from a four year old tree.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to four year old 'Suplumfiftythree' plants grown in the vicinity of Wasco, Kern County, Calif. during 2017 and is believed to apply to plants of the variety grown under similar conditions of soil and climate elsewhere.

TREE

General: (Measurements taken on three-year-old trees unless otherwise noted).

- *Size*.—Medium, reaches a height of approximately 3 meters with normal pruning.
- *Habit*.—Semi-upright.
- *Vigor*.—Medium, top shoot growth of at least 1 meter during the growing season.
- *Productivity*.—Very Productive.
- *Bearer*.—On spurs and long shoots.
- *Fertility*.—Self-incompatible; requires pollinator.
- *Hardiness*.—Hardy in all fruit growing areas of California. Winter chilling requirement is approximately 550 hours at or below 7.2° C.
- *Disease resistance/susceptibility*.—Under close observation in Kern County, Calif., no particular plant/fruit disease resistance/susceptibility has been observed.
- *Insect resistance/susceptibility*.—Under close observation in Kern County, Calif., no particular plant/fruit insect resistance/susceptibility has been observed.

Trunk: (Measurements at approximately 30 cm above soil line on mature tree).

- *Diameter*.—Approximately 13 cm.
- *Texture*.—Medium shaggy, increasing with age of tree.
- *Trunk color*.—About Dark Greyed-Orange 166A, becoming darker with age.

Branches: (Measurements at approximately 90 cm above soil line).

- *Size*.—Diameter approximately 7 cm.
- *Texture*.—Medium shaggy, increasing with age.
- *Color*.—About Dark Grey 201B with highlights of about Medium Greyed-Brown 199B, becoming darker with age.
- *Lenticels*.—Present.
- *Lenticels density*.—Plentiful, about 50/cm$^2$.
- *Lenticels color*.—About Medium Greyed-Green 197C.
- *Lenticels dimensions*.—Length: Approximately 1-3 mm. Width: Approximately 0.5 mm.

Flowering shoots: (Data taken in September at mid-point of current season growth).

- *Size*.—Average diameter approximately 5 mm.
- *Color*.—Topside: About Medium Green 137C, becoming Medium Greyed-Orange 165B by September. Underside: About Medium Green 137C, becoming Medium Greyed-Orange 165B by September.
- *Internode length*.—Approximately 25 mm. Midway on shoot.
- *Flowering shoot lenticels*.—Plentiful. Color: About Medium Greyed-Green 197C. Size: Very small, difficult to see, approximately 0.2 mm.
- *Flowering shoot vegetative buds*.—Size: Medium, approximately 1.5 mm×2.5 mm. Shape: Conical. Bud shape at apex: Acute. Color: About Dark Greyed-Orange 166A.
- *Flowering shoot flower buds*.—Shape: Ovoid. Dimensions: Approximately 1.1 mm×2 mm. Color: About Medium Greyed-Orange 177B. Distribution: 2-6 buds, generally on spurs and one year old shoots.
- *Ratio of flowering buds to vegetative buds*.—2-4 flower buds to 1 vegetative bud.
- *Anthocyanin intensity on upper side of shoot*.—Absent or very sparse.
- *Spur length*.—Medium, usually 8 mm.
- *Position of vegetative bud in relation to shoot*.—Slightly held out.

FOLIAGE

Leaves: (Data taken in September on fully expanded leaves at mid-point of the current season growth).

- *Average length*.—Long; approximately 8.5 cm without petiole.
- *Average width*.—Broad; approximately 4.7 cm.
- *Length/width ratio*.—Moderately elongated, about 1.8:1.
- *Color*.—Upper surface: About Dark Green 139A. Lower surface: About Medium Green 136C.
- *Shape*.—Obovate.
- *Base*.—Acuminate.
- *Margin*.—Crenate.
- *Venation*.—Pinnately net veined.
- *Vein color*.—About Light Green 139D with highlights of Medium Greyed-Orange 176C where exposed to sun.
- *Surface texture*.—Smooth on both upper and lower surfaces.
- *Shape in the cross section*.—Concave.
- *Angle at apex*.—Right angle.
- *Profile*.—Up folded.
- *Leaf blade tip*.—Curved downwardly.
- *Undulation of margin*.—Slight.
- *Glossiness of upper side*.—Medium.
- *Density of pubescence of lower side*.—Absent or very sparse.

Petiole:

- *Average length*.—Medium, approximately 10 mm.
- *Average diameter*.—Approximately 2 mm.
- *Color*.—About Light Green 139D with highlights of Medium Greyed-Orange 176C where exposed to sun.

Stipules:

- *Number/leaf bud*.—Usually one.
- *Typical length*.—Approximately 8 mm.
- *Color*.—About Dark Greyed-Orange 166A when dried.
- *Persistence*.—Falls off.

Leaf glands:

- *Average number and arrangement*.—Mostly a-glandular. Rarely one on petiole.

*Form*.—Globose.
*Diameter*.—Approximately 0.3 mm.
*Color*.—About Medium Greyed-Yellow 162A becoming Dark Greyed-Orange 166A over time.
*Positions of nectarines* (*glands*).—Rarely present, but predominately on the petiole where found.

FLOWERS

General:
*Time of beginning of flowering*.—Medium for the San Joaquin Valley, Calif.
*Flower blooming period*.—First bloom: Approximately February 22 in Wasco, Calif. Full bloom: Approximately February 26 in Wasco, Calif.
*Location of first bloom*.—Tips of one year old shoots.
*Location of full bloom*.—Central part of the tree canopy.
*Duration of bloom*.—Approximately 10 days.
*Diameter of fully opened flower*.—Medium, approximately 1.8 cm.
*Flower form*.—Showy.
Pedicels:
*Length*.—Long, approximately 12 mm.
*Diameter*.—Approximately 1.2 mm.
*Color*.—About Light Green 138C.
*Pubescence*.—Absent.
Petals:
*Number*.—5.
*Arrangement*.—Slightly overlapping.
*Color*.—About White 155A.
*Length*.—Medium, approximately 7.8 mm.
*Width*.—Approximately 7.9 mm.
*Shape*.—Circular.
*Apex shape*.—Rounded.
*Base shape*.—Narrows at point of attachment.
*Surface texture*.—Smooth.
*Undulation of margins*.—Medium.
*Frequency of flowers with double petals*.—None.
*Claw*.—Absent.
Sepals:
*Number*.—5.
*Length*.—Approximately 4 mm.
*Diameter*.—Approximately 3 mm.
*Shape*.—Triangular.
*Color*.—About Light Green 138C.
*Surface texture*.—Smooth.
*Margins*.—Undulating.
*Positioning*.—Adpressed to petals.
*Frequency of flowers with double sepals*.—None.
Stamens:
*Number*.—Usually 24-30, usually 28.
*Average length*.—Variable, ranging from 3 mm to 10 mm.
*Filament color*.—About White 18A.
*Flower pollen color*.—About Medium Yellow-Orange 18A.
*Position*.—Perigynous.
Pistil:
*Average length*.—Approximately 3-4 mm.
*Ovary diameter*.—Approximately 2.2 mm.
*Pubescence*.—Absent.
*Stigma extension in comparison to anthers*.—Usually below.
*Style frequency of supplementary pistils*.—Few.
Receptacle:
*Depth*.—Medium, approximately 4 mm.
*Pubescence of inner surface*.—Absent.
*Pubescence of outer surface*.—Absent.

FRUIT

General: (Description taken near Wasco, Kern County, Calif.).
Ripening:
*Time of beginning of fruit ripening*.—Early season.
*Date of first pick*.—Approximately June 18.
*Date of last pick*.—Approximately June 21.
*Maturity when described*.—Firm.
Size:
*Height*.—Tall, approximately 70 mm.
*Diameter in line with suture plane*.—Approximately 74 mm.
*Diameter perpendicular to suture plane*.—Broad, approximately 74 mm.
*Average weight*.—Large, approximately 140 gm.
Peduncle:
*Length of stem*.—Short, approximately 7 mm.
*Diameter of stem*.—Approximately 3 mm.
*Color of stem*.—About Light Green 139D.
Shape:
*Viewed from apex*.—Circular.
*Viewed in-line with suture*.—Circular.
*Viewed from side, perpendicular to suture*.—Circular.
*Symmetry*.—Symmetric or slightly asymmetric.
*Shape of base*.—Slightly depressed.
*Shape of apex*.—Truncated.
Fruit stem cavity:
*Depth of stalk cavity*.—Shallow; Approximately 6 mm.
*Width of stalk cavity*.—Medium; Approximately 12 mm.
*Depth of suture*.—Absent or very shallow.
Fruit skin:
*Thickness*.—Medium, typical of most varieties.
*Flavor*.—Mildly tart.
*Adherence to flesh*.—Strong.
*Surface texture*.—Smooth, slightly rippled.
*Pubescence*.—None.
*Bloom*.—Medium.
*Ground color*.—Not visible.
*Overcolor*.—About Dark Greyed-Purple 187A, becoming fully Black 202A.
*Relative area of overcolor*.—Whole surface.
*Pattern of overcolor*.—Solid.
*Reticulation*.—Present.
*Tendency to crack*.—Rare.
*Number of lenticels*.—Few, small and difficult to see. About 10/cm$^2$.
*Size of lenticels*.—Very small, less than 0.2 mm.
Flesh:
*Ripens*.—Evenly.
*Texture*.—Crisp-juicy.
*Flavor*.—Mildly sweet, about 34 Brix:Acid.
*Color*.—About Dark Red 45A.
*Firmness*.—Firm, typically 10 lb pressure to harvest.
*Juice*.—Medium, able to squeeze free juice easily.
*Acidity*.—Medium for plums, 0.50% titratable acidity.
*Sweetness*.—High, about 17 degrees Brix at harvest.
*Adherence to stone*.—Adherent.
*Amount of fiber*.—Low.

Fruit use: Fresh market.

Fruit shipping and keeping quality: Good.

Stone:

*Stone freeness*.—Cling.

*Stone size*.—Size: Medium. Length: Approximately 19 mm. Diameter in line with suture plan: Approximately 16 mm. Diameter perpendicular to suture plane: Approximately 7 mm.

*Color*.—About Medium Greyed-Orange 170B when dried.

*Position of maximum diameter*.—Towards stalk end.

*Shape from lateral view*.—Medium elliptic.

*Shape from ventral view*.—Narrow elliptic.

*Shape from basal view*.—Narrow elliptic.

*Base shape*.—Nearly straight.

*Apex shape*.—Pointed.

*Stone ridgers*.—Rounded throughout.

*Stone outgrowing keel*.—Partially developed.

*Ventrical edge*.—Thin with wing toward middle.

*Dorsal edge*.—Narrow, shallow grooves throughout.

*Fibers*.—Not visible.

*Symmetry in lateral view*.—Symmetrical or slightly asymmetrical.

*Texture of lateral surface*.—Slightly rough.

*Width of stalk-end*.—Medium.

*Tendency to split*.—Rare.

What is claimed is:

1. A new and distinct variety of plum tree as herein described and illustrated.

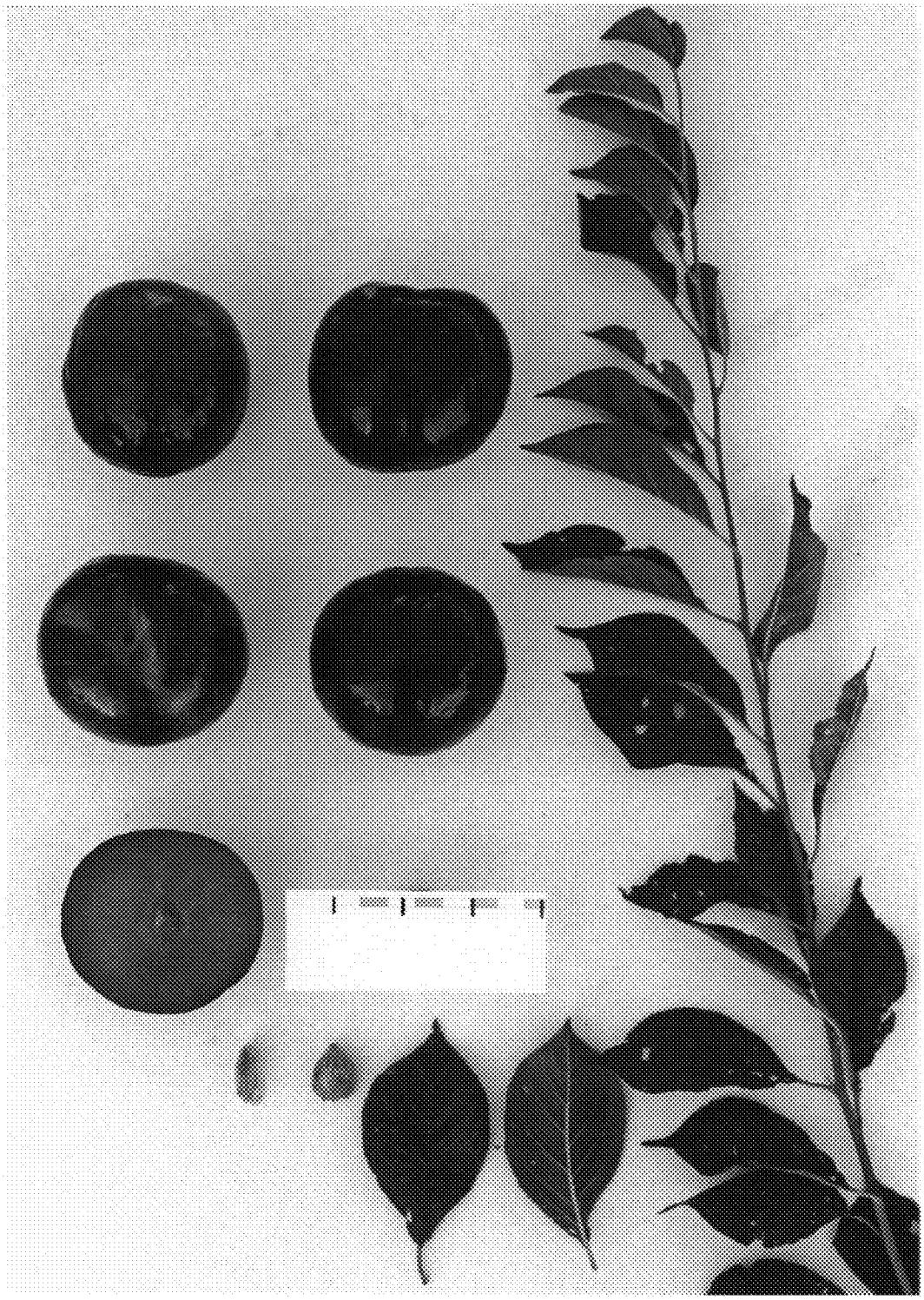

* * * * *